United States Patent [19]

Segre

[11] 4,051,241

[45] Sept. 27, 1977

[54] METHOD OF TREATING DISEASES BY DAILY ADMINISTRATION OF 6-CHLORO-11β,17α,21-TRIHYDROXYPREGNA-1,4,6-TRIENE-3,20-DIONE

[75] Inventor: Eugene J. Segre, Los Altos, Calif.

[73] Assignee: Syntex (U.S.A.) Inc., Palo Alto, Calif.

[21] Appl. No.: 713,769

[22] Filed: Aug. 12, 1976

Related U.S. Application Data

[63] Continuation-in-part of Ser. No. 557,137, March 10, 1975, abandoned.

[51] Int. Cl.$^2$ .............................................. A61K 31/56
[52] U.S. Cl. ................................ 424/243; 260/397.45
[58] Field of Search ..................... 260/397.45; 424/243

[56] References Cited

U.S. PATENT DOCUMENTS 3,232,965 2/1966 Ringold et al. ................. 260/397.45
3,463,852 8/1969 Reimann et al. ...................... 424/243

Primary Examiner—Elbert L. Roberts
Attorney, Agent, or Firm—Gerard A. Blaufarb; William B. Walker

[57] ABSTRACT

This invention relates to a method of treating allergic, dermatologic and rheumatic diseases in mammals which comprises daily orally administering to said mammal in a single dose an effective amount of 6-chloro-11β,17α,21-trihydroxypregna-1,4,6-triene-3,20-dione.

5 Claims, No Drawings

METHOD OF TREATING DISEASES BY DAILY ADMINISTRATION OF 6-CHLORO-11β,17α,21-TRIHYDROXYPREGNA-1,4,6-TRIENE-3,20-DIONE

REFERENCE TO PARENT APPLICATION

This application is a continuation-in-part of application Ser. No. 557,137, filed on Mar. 10, 1975, now abandoned.

BRIEF SUMMARY OF THE INVENTION

This invention relates to a method of treating allergic, dermatologic and rheumatic diseases in mammals which comprises daily orally administering to said mammal in a single dose an effective amount of 6-chloro-11β,17α,21-trihydroxypregna-1,4,6-triene-3,20-dione.

6-Chloro-11β,17α,21-trihydroxypregna-1,4,6-triene-3,20-dione is described in U.S. Pat. No. 3,232,965 as a cortical hormone having a cortisone like (anti-inflammatory) action.

A number of regimens using various corticosteroids are described in the literature. Segre et al., California Medicine, 104: 363–365, May 1966, describe administering a single daily oral morning (8 A.M.) dose of 6α,9α-difluoro-16α-methyl-11β,17ξ,21-trihydroxypregna-1,4-diene-3,20-dione. Myles et al., Ann. Rheum. Dis. (1971), 30, 149–153, describe administering 11β,17α,21-trihydroxypregna-1,4-diene-3,20-dione in a single daily oral morning (10 A.M.) dose nd in divided daily oral doses at 10 A.M. and 10 P.M. Demos et al., Clinical Pharmacology and Therapeutics, Vol. 5, No. 6, Part 1, 721–727, describe administering a single daily oral morning (8 A.M.) dose of 9α-fluoro-11β,17α,16α,21-tetrahydroxypregna-1,4diene-3,20-dione. Carter et al., Ann. Rheum. Dis. (1972), 31, 379–383 describe an alternate-day, single dose oral administration of 11β,17α,21-trihydroxypregna-1,4-diene-3,20-dione.

However, the oral use of corticosteroids in the treatment of mammals, and particularly in human beings, for the treatment of allergic, dermatologic and rheumatic diseases has not been fully practiced because of the deleterious side-effects associated with interference with hypothalamic-pituitary-adrenal (HPA) axis function during long term administration of the corticosteroid; and because suppression of the HPA axis increases in relation to corticosteroid dose, frequency and duration of treatment. Moreover, potent corticosteroids with an extended biological half-life have a more prolonged effect on the HPA axis due to their presence in the body, which presence does not permit normal cortisol levels to return. I have found, as shown by Example 1, that 6-chloro-11β,17α,21-trihydroxypregna-1,4,6-triene-3,20-dione has a plasma cortisol half-life of about 120 minutes, which half-life is relatively short as compared to other corticosteroids. The plasma cortisol half-lives of certain corticosteroids, including 6-chloro-11β,17α,21-trihydroxypregna-1,4,6-triene-3,20-dione, are tabulated in Table I which follows:

TABLE I

| Compound | Plasma Half-Life in Minutes |
| --- | --- |
| Prednisolone (11β,17α,21-trihydroxypregna-1,4-diene-3,20-dione) | 200 or greater[a] |
| 9α-Fluoro-16α-hydroxyprednisolone (9α-fluoro-11β,16α,17α,21-tetrahydroxypregna-1,4-diene-3,20-dione) | 200 or greater[a] |
| 9α-Fluoro-16β-methylprednisolone (9α-fluoro-16β-methyl-11β,17α,21-trihydroxypregna-1,4-diene-3,20-dione) | 300 or greater[a] |
| 9α-Fluoro-16α-methylprednisoline (9α-fluoro-16α-methyl-11β,17α,21-trihydroxypregna-1,4-diene-3,20-dione) | 300 or greater[a] |
| 6-Chloro-Δ⁶-prednisolone (6-chloro-11β,17α,21-trihydroxypregna-1,4,6-triene-3,20-dione) | 120[b] |

[a]Melby, Ann. Int. Med., 81:505–512 (see p. 508), 1974
[b]Determined according to the procedure set forth in Example 1.

It has now surprisingly been found that the unwanted side-effects associated with HPA axis suppression, as measured by maintenance of normal plasma cortisol levels, normal metyrapone (METP) response and normal insulin hypoglycemia (IHT) response, are not present when 6-chloro-11β,17α,21-trihydroxypregna-1,4,6-triene-3,20-dione is administered, as shown more fully in Example 2 below.

In addition, as shown in Example 3 below, adverse metabolic effects, namely, loss of nitrogen and calcium, are minimized when 6-chloro-11β,17α,21-trihydroxypregna-1,4,6-triene-3,20-dione, as compared to prednisolone (11β,17α,21-trihydroxypregna-1,4-diene-3,20-dione), is administered.

In the practice of this invention a therapeutically effective amount of 6-chloro-11β,17α,21-trihydroxypregna-1,4,6-triene-3,20-dione is administered to the mammal, and particularly human being, afflicted with an allergic, dermatologic or rheumatoid disease, on a daily basis in a single dose. The preferred amount administered is from about 2.5 mg. to about 20 mg. per day, and most preferably from about 2.5 mg. to about 12.5 mg. per day. In addition, the daily dosage of 6-chloro-11β,17α,21-trihydroxypregna-1,4,6-triene-3,20-dione is preferably administered in the morning.

Daily morning administration of 6-chloro-11β,17α,21-trihydroxypregna-1,4,6-triene-3,20-dione, rather than daily afternoon or evening administration, is preferred because it is less suppressive to the HPA axis. The lessened suppression achieved by daily morning administration of a single dose is because there is less interference with the diurnal pattern of endogenous corticosteroid secretion; and less interference with ACTH production, which is particularly sensitive to the presence of exogenous corticosteroids during the nocturnal hours.

In all cases, administration of 6-chloro-11β,17α,21-trihydroxy-pregna-1,4,6-triene-3,20-dione, for the purpose set forth herein, should be consistent with the best and/or accepted medical (or veterinary) practices so as to maximize the benefits to the subject.

In the practice of the present invention, a therapeutically effective amount of 6-chloro-11β,17α,21-trihydroxypregna-1,4,6-triene-3,20-dione or a pharmaceutical composition containing it, is daily orally administered to the mammal in a single does upon arising.

6-Chloro-11β,17α,21-trihydroxypregna-1,4,6-triene-3,20-dione can be administered either singly or in combination with another compound or compounds, or other pharmaceutical agents, carriers, adjuvants, etc. 6-Chloro-11β,17α,21-trihydroxypregna-1,4,6-triene, or compositions containing it, can be administered either in the form of solid, semi-solid, or liquid dosage forms. Typically, administration is by a pharmaceutical composition containing 6-chloro-11β,17α,21-trihydroxypregna-1,4-diene-3,20-dione and one or more pharmaceutical carriers or adjuvants.

The administerable pharmaceutical composition may take the form of oral tablets, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, sucrose, magnesium carbonate, and the like. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution of suspension. If desired the pharmaceutical composition to be administered may also contain minor amounts of non-toxic auxiliary substances such as wetting or emulsifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's *Pharmaceutical Sciences*, Mack Publishing Company, Easton, Pa. 14th Edition, 1970. The composition or formulation to be administered is adapted to provide a daily oral single dose of an effective amount of 6-chloro-11$\beta$,17$\alpha$,21-trihydroxypregna-1,4,6-triene-3,20-dione, usually from about 2.5 to about 20 mg., for treating the allergic, dermatologic or rheumatoid disease.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE 1

Half-Life of 6-Chloro-11$\beta$,17$\alpha$,21-Trihydroxypregna-1,4,6-Triene-3,20-Dione Two mg. of 6-chloro-11$\beta$,17$\alpha$,21-trihydroxypregna-1,4,6-triene-3,20-dione containing 100 $\mu$c of tritium-label were administered intravenously to two human volunteers following an overnight fast. The plasma of each volunteer was analyzed for organic solvent extractable radioactivity over a 24 hour period.

Subsequently, the above procedure was repeated on the same two volunteers except that 2 mg. of 6-chloro-11$\beta$,17$\alpha$,21-trihydroxypregna-1,4,6-triene-3,20-dione containing 100 $\mu$c of tritium-label was administered orally, rather than intravenously.

Based upon the rate of disappearance of organic solvent extractable radioactivity, representing unchanged 6-chloro-11$\beta$,17$\alpha$,21-trihydroxypregna-1,4,6-triene-3,20-dione, it was found that there was essentially no difference between oral and intravenous administration; and the half-life of 6-chloro-11$\beta$,17$\alpha$,21-trihydroxypregna-1,4,6-triene-3,20-dione for volunteer No. 1 was approximately 110 minutes and of volunteer No. 2 was approximately 125 minutes, giving an average of approximately 120 minutes.

EXAMPLE 2

Comparison Of The Effect of 6-Chloro-11$\beta$,17$\alpha$,21-Trihydroxy-1,4,6-Triene-3,20-Dione And Other Corticosteroids On HPA-Axis Function After 6 A.M. Administration For 7 Days Each of 39 normal human subjects was hospitalized on a clinical pharmacology ward for the entire time (14 days) while the procedures described herein were carried out.

The following tests were performed, except as otherwise indicated in Table II below, on each of the subjects:

1. Fasting plasma cortisol level at 6 A.M. on each of days 1–14, according to the method of Murphy et al., J. Clin. Endocr. 23:293, 1963, which is hereby incorporated by reference and made a part hereof.

2. Insulin hypoglycemia test (IHT), according to the method described by Greenwood, et al., J. Clin. Invest. 45:429, 1966, which is hereby incorporated by reference and made a part hereof, on day two (pre-administration of drug) and day 12 (post-administration of drug).

3. Metyrapone (METP) test, according to a modification of the method described by Liddle et al., J. Clin. Endocr. 19:875, 1959, which is hereby incorporated by reference and made a part hereof, on days three and four (pre-administration of drug) and on days 13 and 14 (post-administration of drug). The urine of each of the subjects was collected at 6 hour intervals during the entire 14 day period and analyzed for 17-ketogenic steroids for the METP test.

On each of days 5–11 the various corticosteroids were orally administered, all subjects receiving their daily single dosage of corticosteroids at 6 A.M. Tabulated below, in Table II, are the numbers of subjects receiving a particular dosage per day of a particular corticosteroid. The dosage regimens chosen reflect the relative potencies of the corticosteroids tested. Thus, for example, 12.5 mg. of 6-chloro-11$\beta$,17$\alpha$,21-trihydroxypregna-1,4,6-triene-3,20-dione is equipotent to 25.0 mg. of 11$\beta$,17$\alpha$,21-trihydroxypregna-1,4-diene-3,20-dione, 6.0 mg. of 9$\alpha$-fluoro-16$\alpha$-methyl-11$\beta$,17$\alpha$,21-trihydroxypregna-1,4-diene-3,20-dione or 6.5 mg. of 9$\alpha$-fluoro-16$\beta$-methyl-11$\beta$,17$\alpha$,21-trihydroxypregna-1,4-diene-3,20-dione.

TABLE II

| Corticosteroid | Milligrams Per Day | Number of Subjects |
| --- | --- | --- |
| 6-Chloro-11$\beta$,17$\alpha$,21-trihydroxy-pregna-1,4,6-triene-3,20-dione | 2.5 | 3 |
|  | 5.0 | 3 |
|  | 12.5 | 4 |
| 11$\beta$,17$\alpha$,21-trihydroxypregna-1,4-diene-3,20-dione | 5.0 | 3 |
|  | 10.0 | 3 |
|  | 25.0 | 3 |
| 9$\alpha$-fluoro-16$\alpha$-methyl-11$\beta$,17$\alpha$,21-trihydroxypregna-1,4-diene-3,20-dione | 0.5 | 5 |
|  | 3.75 | 3 |
|  | 6.0 | 3 |
| 9$\alpha$-fluoro-16$\beta$-methyl-11$\beta$,17$\alpha$,21-trihydroxypregna-1,4-diene-3,20-dione | 2.0 | 3 |
|  | 4.0 | 3 |
|  | 6.5 | 3 |

The insulin hypoglycemia tests (IHT), metyrapone (METP) tests and plasma cortisol levels for each of the subjects, prior to drug administration, were found to be normal.

By comparing the results obtained on days two (pre-administration of drug) and 12 (post-administration of drug) in the insulin hypoglycemia test (IHT), it is determined if a normal response has been maintained following drug administration.

By comparing the results obtained on days three and four (pre-administration of drug) and 13 and 14 (post-administration of drug), in the metyrapone (METP) test it is determined if a normal response has been maintained following drug administration.

By comparing the results obtained on days one and two (preadministration) and days 11 and 12 (post-administration) for plasma cortisol levels, it is determined if a normal response has been maintained following drug administration.

The results of the tests described above for the various corticosteroids at the various dosage levels, set forth in Table II above, are as follows:

TABLE III

| Corticosteroid | Dose (Milligrams Per Day) | Normal/Total IHT Response | Normal/Total METP Response | Normal/Total A. M. Plasma Cortisol |
|---|---|---|---|---|
| 6-chloro-11β,17α,21-trihydroxy- | 2.5 | — | — | 3/3 |
| pregna-1,4,6-triene-3,20-dione | 5.0 | — | — | 3/3 |
|  | 12.5 | 4/4 | 4/4 | 3/4 |
| 11β,17α21-trihydroxypregna- | 5.0 | — | — | 3/3 |
| 1,4-diene-3,20-dione | 10.0 | — | — | 3/3 |
|  | 25.0 | 2/3 | 3/3 | 0/3 |
| 9α-fluoro-16α-methyl-11β,17α, | 0.5 | 1/2 | 3/4 | 1/5 |
| 21-trihydroxypregna-1,4-diene- | 3.75 | 0/3 | 0/3 | 0/3 |
| 3,20-dione | 6.0 | 0/2 | 0/3 | 0/3 |
| 9α-fluoro-16β-methyl-11β,17α, | 2.0 | 0/3 | 0/3 | 0/3 |
| 21-trihydroxypregna-1,4-diene- | 4.0 | 0/3 | 0/3 | 0/3 |
| 3,20-dione | 6.5 | 0/3 | 0/3 | 0/3 |

From Table III it will be observed that the plasma cortisol levels of all subjects administered 2.5 and 5.0 mg. of 6α-chloro-11β,17α,21-trihydroxypregna-1,4,6-triene-3,20-dione remained normal and three out of four subjects administered 12.5 mg. remained normal. Of the three subjects administered 25 mg. of 11β,17α,21-trihydroxypregna-1,4-diene-3,20-dione, a dose with an anti-inflammatory potency approximately equal to 12.5 mg. of 6-chloro-11β,17α,21-trihydroxypregna-1,4,6-triene-3,20-dione, none maintained normal plasma cortisol levels. Of the nine subjects administered 9α-fluoro-16β-methyl-11β,17α,21-trihydroxypregna-1,4-diene-3,20-dione only one, at the lowest dose administered, maintained normal plasma cortisol levels. Of the nine subjects administered 9α-fluoro-16β-methyl-11β,17α,21-trihydroxypregna-1,4-diene-3,20-dione, none maintained normal plasma cortisol levels.

Further, it is readily apparent from Table III that all subjects receiving 12.5 mg. of 6-chloro-11β,17α,21-trihydroxypregna-1,4,6-triene-3,20-dione maintained a normal response to the metyrapone test. Of the 10 subjects administered 9α-rfluoro-16α-methyl-11β,17α,21-trihydroxypregna-1,4-diene-3,20-dione, only three of the four receiving 0.5 mg. (the lowest dose, with an anti-inflammatory potency approximately equal to 2.5 mg. of 6-chloro-11β,17α,21-trihydroxypregna-1,4,6-triene-3,20-dione) showed a normal metyrapone test. Of the nine subjects administered 9α-fluoro-16β-methyl-11β,17α,21-trihydroxypregna-1,4-diene-3,20-dione, none showed a normal metyrapone test.

Still further, it is readily discernible from Table III that all subjects receiving 12.5 of 6-chloro-11β,17α,21-trihydroxypregna-1,4,6-triene-3,20-dione maintained a normal response to the insulin hypoglycemia test. Of the three subjects administered an equipotent dose, 25 mg., of 11β,17α,21-trihydroxy-1,4-pregnadine-3,20-dione only two maintained a normal response to the insulin hypoglycemia test. Of the seven subjects administered 9α-fluoro-16α-methyl-11β,17α,21-trihydroxypregna-1,4-diene-3,20-dione, only one remained normal in the insulin hypoglycemia test and that at the lowest dose of 0.5 mg., which has an anti-inflammatory potency of approximately 2.5 mg. of 6-chloro-11β,17α,21-trihydroxypregna-1,4,6-triene-3,20-dione. Of the nine subjects administered 9α-fluoro-16β-methyl-11β,17α,21-trihydroxypregna-1,4-diene-3,20-dione, none maintained a normal response to the insulin hypoglycemia test.

EXAMPLE 3

Comparison of Metabolic Effects (Loss of Nitrogen and Calcium) of

6-Chloro-11β,17α,21-Trihydroxypregna-1,4,6-Triene-3,20-Dione and

11β,17α,21-Trihydroxypregna-1,4-Diene-3,20-Dione

Four normal subjects were admitted to a hospital metabolic ward and maintained on a constant diet for days 1–3, the equilibration period.

On days 4–9, the control period, the subjects were also kept on the same constant diet and their urine was collected every 24 hours and assayed for nitrogen and calcium, determined fluorometrically using the method of Henry, R. J., Clinical Chemistry Principles and Techniques, 3rd Edition, p. 293, 1965, which reference is hereby incorporated by reference and made a part hereof.

On days 10–15, the treatment period, the subjects were still kept on the same constant diet, and 20 mg. (three subjects, 1, 2 and 3) and 12.5 mg. (one subject, 4) of 6-chloro-11β,17α,21-trihydroxypregna-1,4-diene-3,20-dione were daily orally administered in a single dose. The urine of the subjects was collected every 24 hours and assayed for nitrogen and calcium.

The results obtained are reported in Table IV.

TABLE IV

| Subject | 6-chloro-11β,17α22-trihydroxypregna-1,4-6-triene-3,20-dione Administered Orally Daily on Days 10-15 | Mean Urinary Nitrogen[1] | | | Mean Urinary Calcium[2] | | |
|---|---|---|---|---|---|---|---|
| | | Control Period Days 4–9 | Treatment Period Days 10–15 | Change Between Control and Treatment Periods | Control Period Days 4–9 | Treatment Period Days 10–15 | Change Between Control and Treatment Periods |
| 1 | 20 mg. | 5.1 | 4.9 | −0.2 | 142 | 170 | +28 |
| 2 | 20 mg. | 4.1 | 4.3 | +0.2 | 140 | 180 | +40 |

TABLE IV-continued

| | 6-chloro-11β,17α22-trihydroxypregna-1,4-6-triene-3,20-dione Administered Orally Daily on | Mean Urinary Nitrogen[1] | | | Mean Urinary Calcium[2] | | |
|---|---|---|---|---|---|---|---|
| Subject | Days 10–15 | Control Period Days 4–9 | Treatment Period Days 10–15 | Change Between Control and Treatment Periods | Control Period Days 4–9 | Treatment Period Days 10–15 | Change Between Control and Treatment Periods |
| 3 | 20 mg. | 6.7 | 8.1 | +1.4 | 146 | 154 | +8 |
| 4 | 12.5 mg. | 12.0 | 11.8 | −0.2 | 271 | 244 | −27 |

[1]Expressed in grams per 24 hours
[2]Expressed in milligrams per 24 hours.

After 8 weeks had elapsed, subjects 1 and 2 were readmitted to the hospital metabolic ward. The same procedures were followed as detailed above except that the constant diet of both subjects was insignificantly modified from that used during their first admission and the same modified constant diet was fed throughout the readmission period and both subjects were orally daily administered a single dose of 40 mg. of 11β,17α,21-trihydroxypregna-1,4-diene-3,20-dione, in place of the equipotent dose of 20 mg. of 6-chloro-11β,17α,21-trihydroxypregna-1,4,6-triene-3,20-dione, on days 10–15, the treatment period. The results are reported in Table IVA.

TABLE IVA

| | 11β,17α,21-trihydroxypregna-1,4-diene-3,20-dione Administered Orally Daily on | Mean Urinary Nitrogen[1] | | | Mean Urinary Calcium[2] | | |
|---|---|---|---|---|---|---|---|
| Subject | Days 10–15 | Control Period Days 4–9 | Treatment Period Days 10–15 | Change Between Control and Treatment Periods | Control Period Days 4–9 | Treatment Period Days 10–15 | Change Between Control and Treatment Periods |
| 1 | 20 mg. | 7.9 | 9.6 | +1.7 | 196 | 273 | +77 |
| 2 | 20 mg. | 8.2 | 9.4 | +1.2 | 205 | 274 | +69 |

[1]Expressed in grams per 24 hours.
[2]Expressed in milligrams per 24 hours.

From "Change Between Control and Treatment Periods" in Tables IV and IVA it is manifest that there is a greater loss of both nitrogen and calcium when 11β,17α,21-trihydroxypregna-1,4-diene-3,20-dione is administered, as compared to an equipment dose of 6-chloro-11β,17α,21-trihydroxypregna-1,4,6-triene-3,20-dione, to subjects 1 and 2.

EXAMPLE 4

| Ingredients | Quantity per tablet, mgs. |
|---|---|
| 6-chloro-11β,17α,21-trihydroxypregna-1,4,6-triene-3,20-dione | 12.5 |
| cornstarch (paste) | 50 |
| magnesium stearate | 0.8 |
| lactose | to 500 |

The above ingredients are thoroughly mixed and pressed into single scored tablets.

Similarly tablets containing 2.5, 5.0 and 10.0 mg. of 6-chloro-11β,17α,21-trihydroxypregna-1,4,6-triene-3,20-dione are prepared.

EXAMPLE 5

| Ingredients | Quantity per tablet, mgs. |
|---|---|
| 6-chloro-11β,17α,21-trihydroxypregna-1,4,6-triene-3,20-dione | 12.5 |
| cornstarch | 38 |
| magnesium stearate | 0.76 |
| polyvinylpyrrolidone | 17 |
| lactose | to 380 |

The above ingredients are mixed intimately and pressed into single scored tablets.

Similarly tablets containing 2.5, 5.0 and 10.0 mg. of 6-chloro-11β,17α,21-trihydroxypregna-1,4,6-triene-3,20-dione are prepared.

EXAMPLE 6

| Ingredients | Quantity per capsule, mgs. |
|---|---|
| 6-chloro-11β,17α,-21-trihydroxypregna-1,4,6-triene-3,20-dione | 12.5 |
| cornstarch | 38 |
| lactose | to 380 |

The above ingredients are mixed and introduced into a hard-shell gelatin capsule.

Similarly gelatin capsules containing 2.5, 5.0 and 10.0 mg. of 6-chloro-11β,17α,21-trihydroxypregna-1,4,6-triene-3,20-dione are prepared.

EXAMPLE 7

| Ingredients | Quantity per capsule, mgs. |
|---|---|
| 6-chloro-11β,17α,21-trihydroxypregna-1,4,6-triene-3,20-dione | 5.0 |
| lactose | 72 |
| magnesium stearate | 8 |

The above ingredients are mixed and introduced into a hard-shell gelatin capsule.

Similarly gelatin capsules containing 2.5, 10.0 and 12.5 mg. of 6-chloro-11β,17α-21-hydroxypregna-1,4,6-triene-3,20-dione are prepared.

In its most preferred aspect this invention relates to the method of treating allergic, dermatologic and rheumatic diseases in mammals while, at the same time, lessening the deleterious side effects associated with the hypothalamic-pituitary-adrenal (HPA) axis function during corticosteroid administration, which comprises daily orally administering to said mammal in a single dose in the morning an effective amount of from about 2.5 mg. to about 20 mg. of the compound 6-chloro-11β,17α,21-trihydroxypregna-1,4,6-triene-3,20-dione.

What is claimed is:

1. The method of treating allergic, dermatologic and rheumatic diseases in mammals while, at the same time, lessening the deleterious side effects associated with the hypothalamic-pituitary-adrenal (HPA) axis function during corticosteroid administration, which comprises daily orally administering to said mammal in a single dose in the morning an effective amount of from about 2.5 mg. to about 20 mg. of the compound 6-chloro-11β,17α,21-trihydroxypregna-1,4,6-triene-3,20-dione.

2. The method of claim 1 in which said effective amount is from about 2.5 to about 12.5 mg.

3. The method of claim 2 in which said mammal is a human being and the allergic disease is asthma.

4. The method of claim 3 in which said mammal is a human being and the rheumatic disease is rheumatoid arthritis.

5. A therapeutic composition useful for treating allergic, dermatologic and rheumatic diseases in mammals while, at the same time, lessening the deleterious side effects associated with the hypothalamic-pituitary-adrenal (HPA) axis function during corticosteroid administration, adapted to provide a daily oral single morning dose of an effective amount of from about 2.5 mg. to about 20 mg. of the compound 6-chloro-11β,17α,21-trihydroxypregna-1,4,6-triene-3,20-dione.

* * * * *